United States Patent [19]
Tsubota et al.

[11] Patent Number: 6,146,630
[45] Date of Patent: *Nov. 14, 2000

[54] INHIBITORS FOR THE ADHESION OF LYMPHOCYTES TO GLANDULAR CELLS

[76] Inventors: Kazuo Tsubota, 26-7, Nishifuna 5-chome, Funabashi-shi, Chiba; Tsutomu Takeuchi, 9-9, Magamoto 5-chome, Urawa-shi, Saitama, both of Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/946,838

[22] Filed: Oct. 8, 1997

[30] Foreign Application Priority Data

Feb. 10, 1997 [JP] Japan ................................... 9-026298

[51] Int. Cl.$^7$ ......................... A61K 39/395; C07K 16/28
[52] U.S. Cl. ..................... 424/153.1; 424/152.1; 424/158.1; 530/388.22; 530/388.23; 530/388.7
[58] Field of Search ............................ 424/153.1, 152.1, 424/158.1; 530/388.22, 388.23, 388.7

[56] References Cited

U.S. PATENT DOCUMENTS 5,610,281  3/1997  Brenner et al. .

OTHER PUBLICATIONS

Yang et al. J. of Autoimmunity 7: 859, 1994.
Hayashi et al. Clin Exp. Immunol. 102: 360, 1995.
Saito et al. J. of Clin. Lab Analysis 7: 180 1993.
Fox et al. In *Textbook of Rheumatology* 1993 Ed By Kelley et al. W. B. Saunders Co pp. 931–942.
Russell et al. Eur. J. Immunol. 24: 2832, 1994.
Caul: et al. Annals of Rheumatic Disease 54: 209, 1995.
K. L. Cepek, et al., "Integrin $\alpha^E \beta 7$ Mediates Adhesion of T Lymphocytes to Epithelial Cells", *The Journal of Immunology*, vol. 150, 3459–3470, No. 8, Apr. 15, 1993.
K. L. Cepek, et al., "Adhesion between eithellal cells and T lymphhocytes mediated by E–cadherin and the $\alpha^E \beta_7$ Integrin", *Nature*, vol. 372, 190–193, Nov. 10, 1994.
Russell, G. et al., "Distinct structural and functional epitopes of the $\alpha^E \beta_7$ integrin", *Eur. J. Immunol.*, 1994, 24: 2832–2841.

*Primary Examiner*—Christina Y. Chan
*Assistant Examiner*—Martha Lubet
*Attorney, Agent, or Firm*—Oliff & Berridge, PLC

[57] ABSTRACT

The present invention provides adhesion inhibitors for suppressing the adherence between E-cadherin of glandular cells and integrin of lymphocytes. Sjôgren's syndrome comprises disorders wherein secretory glands such as lacrimal gland are destroyed by autoimmunity, and the adherence of CD8$^+$ T cells to the surface of acinar cells is observed by the immunohistological analysis of lacrimal gland from patients. Integrin on the surface of T cells and E-cadherin on the surface of acinar cells play a major role in the mechanism of adhesion between these cells, while the adherence of T cells to acinar cells is reduced using anti-E-cadherin and anti-integrin antibodies. Sjôgren's syndrome, such as autoimmune adenitis, can be treated using these antibodies.

9 Claims, 1 Drawing Sheet

INHIBITORS FOR THE ADHESION OF LYMPHOCYTES TO GLANDULAR CELLS

BACKGROUND OF THE INVENTION

1. Field of the Invention

The present invention relates to an inhibitor for the adhesion of lymphocytes to glandular cells which causes autoimmune adenitis such as that in Sjôgren's syndrome.

2. Description of the Related Art

In general, immunocytes play an important role in protecting self systems from the invasion of foreign substances, etc. That is, with an invasion of foreign substances such as microorganisms, immunocytes such as T lymphocytes recognize these foreign substances and produce appropriate cytokines. Cytokines thus produced activate specific T cells. These activated T cells secrete cytotoxic substances to destroy the foreign substances and eliminate them from the inside of body. Thus, immunocytes distinguish between self systems and non-self foreign substances to destroy only the latter. This ability to distinguish between self system from non-self foreign substance is mainly based on the structure of proteins, etc. on the cell surface.

Although immunocytes primarily distinguish self from non-self and destroy only non-self, recently it has become evident that these immunocytes for unaccountable reasons erroneously recognize self system as foreign substance and destroy the self system, causing various disorders (autoimmune diseases).

For example, one of these autoimmune diseases is Sjôgren's syndrome. As symtoms of this syndrome include symptoms such as dry eye due to alacrima, sialaporia, etc., manifestation due to some gland abnormality has been indicated to stimulate investigation along that line. As a result, it has become evident that Sjôgren's syndrome is manifested by the destruction of secretory glands such as lacrimal and salivary glands by self immunocytes.

Although in Sjôgren's syndrome the target self system of self immunocytes is evidently secretory glands such as lacrimatory gland, salivary gland, etc., the action mechanism of destroying target cells, that is, how immunocytes recognize, bind and destroy these target cells has not been ascertained.

On the other hand, the adhesion factor of immunocytes, more specifically that of lymphocytes involved in binding to intestinal epithelial cells, has been discovered [see The Journal of Immunology, 150, 3459–3470 (1993)]. Furthermore, the ligand of that adhesion factor has been identified as E-cadherin expressed on the epithelial cells of small intestine (Nature, 372: 190–193, 1994).

In view of these situation, the present inventors carefully studied to ascertain adhesion factors of glandular cells and immunocytes, and, based on each adhesion factor herein discovered, developed adhesion inhibitors which suppress the binding between these adhesion factors.

SUMMARY OF THE INVENTION

As described above, the present inventors attempted to elucidate adhesion factors of glandular cells and immunocytes. As a result, they found that E-cadherin on the surface of glandular cells and integrin $\alpha^E\beta_7$ on the surface of immunocytes are involved in their adhesion, further indicating a possibility that lymphocytes belonging to immunocytes adhere to glandular cells by way of the adhesion between these adhesion factors, destroying glandular cells by the destructive action of said lymphocytes to manifest autoimmune adenitis such as Sjôgren's syndrome.

Based on the above discovery, an inhibitor for the adhesion between glandular cells and lymphocytes of the present invention prevents said adhesion to cause autoimmune adenitis by suppressing the adhesion between E-cadherin of glandular cells and integrin $\alpha^E\beta_7$ of lymphocytes.

Therefore, the present invention may be applied for the therapy of the autoimmune adenitis by inhibiting the adhesion between E-cadherin of glandular cells and integrin $\alpha^E\beta_7$ of lymphocytes which cause the autoimmune adenitis.

More specifically, said glandular cells include epithelial cells of lacrimal as well as salivary glands, and the autoimmune adenitis wherein these glandular cells become the target for lymphocytes includes adenitis in Sjôgren's syndrome. Dry eye (alacrima) and sialaporia are well known symptoms of adenitis. Dry eye (alacrima) and sialaporia are known as clinical symptoms of adenitis in this Sjôgren's syndrome.

Therefore, the adhesion inhibitor of the present invention may be preferably applied for the treatment of various symptoms in the above described Sjôgren's syndrome.

Inhibitors for adhesion of the present invention comprise, for example, antibodies acting on the site involved in the adhesion of E-cadherin of glandular cells or integrin $\alpha^E\beta_7$ of lymphocytes (hereafter referred to as adhesion site). These antibodies include, in addition to those recognizing the adhesion site and binding directly to it, those not directly binding to the adhesion site but to an other site to mask the former site, and those altering the three dimensional structure of adhesion factors to prevent their binding. In addition, these antibodies may be polyclonal or monoclonal.

In order to apply the above described adhesion inhibitors in pharmaceutic or prophylactic drugs, it is necessary to mix them with pharmacologically acceptable excipients prior to use.

DESCRIPTION OF PREFERRED EMBODIMENTS

Figure 1:
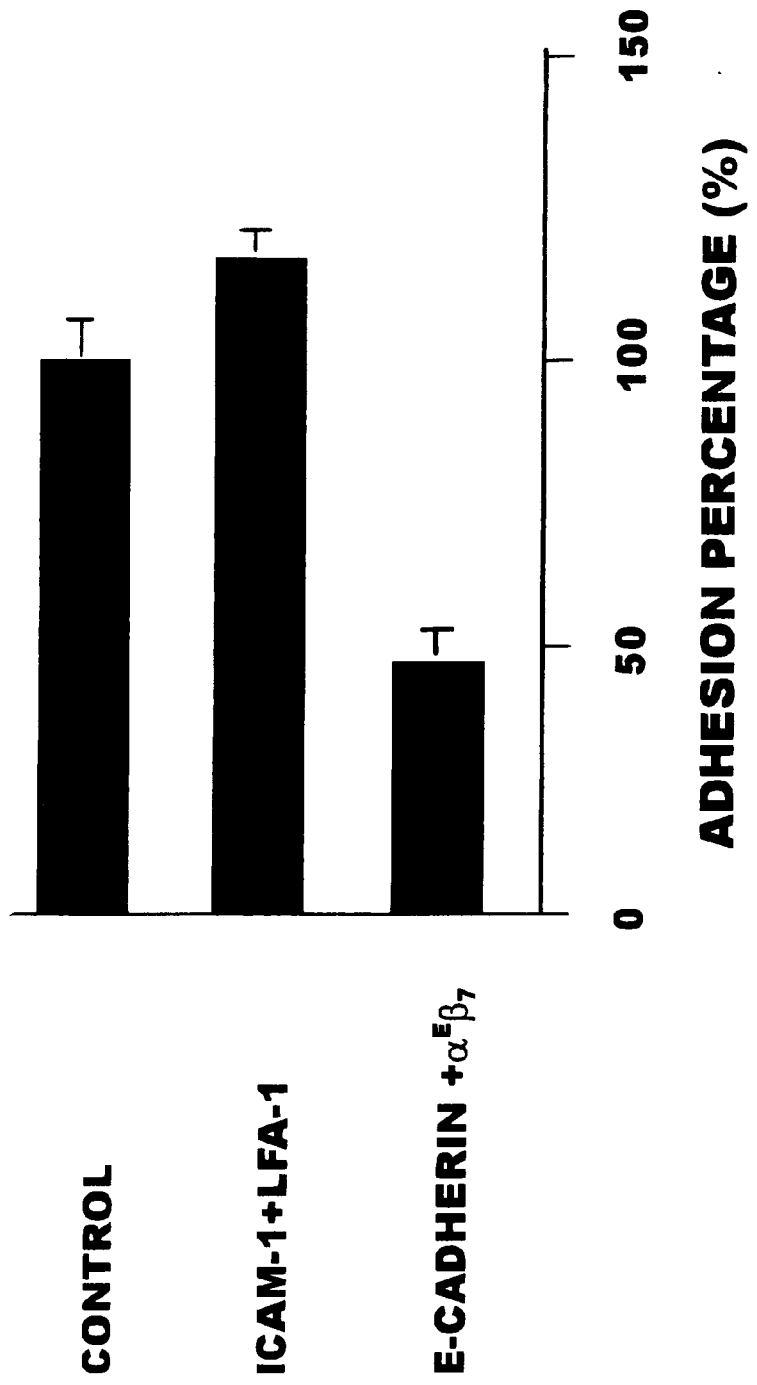
FIG. 1 is a graphical representation showing the inhibition of adhesion between glandular cells and lymphocytes using anti-integrin $\alpha^E\beta_7$ antibody and anti-E-cadherin antibody.

In the following, preferred embodiments of the present invention will be described with reference to the drawing.

Inhibitors for the adhesion between glandular cells and lymphocytes suppress the adhesion between integrin on the surface of lymphocytes and E-cadherin on the surface of glandular cells.

Inhibition by these adhesion inhibitors is exerted by modifying the adhesion site for integrin or cadherin. This modification includes the destruction of the adhesion site, the addition of other molecule to said site or the alteration of the three-dimensional structure of adhesion factors. Any one of these modifications may be applied, but a modification enabling the inhibition of adhesion between the above mentioned cells without deteriorating lymphocyte's function is preferable. Also, for the sake of convenience, for example, modification by adding antibodies is preferred.

Concretely, for the modification of adhesion factors, the use of antibodies which directly (specifically) recognizes the adhesion site for one of them is preferred. Antibodies which do not recognize said adhesion site but mask it by recognizing and binding to its surrounding structure may also be used. Furthermore, antibodies which modify the three dimensional structure of adhesion factors by binding even to a site remote from the adhesion site may also be used. Due to the high site-specificity, these antibodies specifically inhibit the adhesion between these cells without damaging other cell functions.

These antibodies may be either monoclonal or polyclonal. Monoclonal antibodies can be produced according to the standard method from hybridomas formed by fusing spleen cells of mice immunized with said adhesion factor as antigen with B-cell tumor line. Polyclonal antibodies can be obtained by periodically immunizing an appropriate host with said adhesion factor as antigen. There is no particular limitation in host animal species used. Activity of antibodies thus produced in inhibiting the adhesion between lymphocytes and glandular cells is confirmed by the immunofluorescence staining technique as described below.

In order to make pharmaceutials for the autoimmune adenitis from the above described adhesion inhibitors, it is necessary to add to them vehicles (excipients), which can be selected depending on the final dosage form. For example, for injection, the above described adhesion inhibitors may be mixed with sterile solvents. In addition, since biological products are generally unstable, preservatives may be added if necessary.

In the following, while the present invention will be described with reference to the preferred embodiments, it is to be understand that the true scope of the invention is not to be limited to them.

EXAMPLES

Example 1
Elucidation of Adhesion Factors of Glandular Cells and Lymphocytes

Since the adhesion of T cells to the target glandular cells is essential for exerting the cytotoxicity of the former, the adhesion factors are expected to be involved in this adhesion. Therefore, the inventors first aimed at elucidating these adhesion factors.

In view of the fact that E-cadherin discovered in small intestine epithelial cells and presumably involved in the homophylic adhesion has been recently found to adhere to integrin $\alpha^E\beta_7$ [Nature (1994), 372, 190–193], adhesion factors have been analyzed according to the following procedures.

1) Distribution of surface proteins on lacrimal gland tissue cells

Surface proteins were analyzed by an immunofluorescence staining technique using antibodies raised against various proteins. Samples used were sections of lacrimal gland tissue excised by biopsy underwent to patients with Sjôgren's syndrome. Antibodies used included anti-CD4 antibody, anti-CD8 antibody, anti-integrin $\alpha^E\beta_7$ antibody, anti-ICAM-1 (intercellular adhesion molecule-1) antibody, anti-LFA-1 (lymphocyte function-associated antigen-1) antibody, anti-HLA-DR (human leukocyte antigen-DR) antibody and anti-E-cadherin antibody.

Herein ICAM-1 is an adhesion factor distributed in various glandular cells. LFA-1 is present on lymphocytes and known to adhere to ICAM-1. Furthermore, HAL-DR is a molecule expressed on the surface of lacrimal glandular cells and known to be recognized by CD4$^+$ T cells.

Immunofluorescence staining technique was carried out as follows.

Plural tissue sections were prepared from frozen lacrimal gland tissues, and fixed in acetone for about 10 min. After washing with phosphate buffered saline (PBS) three times for 5 min each, they were blocked in PBS containing 10% normal goat serum for 10 min. Next, one of the above described antibodies was selected as the primary antibody. This antibody was properly diluted and reacted with each section overnight at 4° C. Next, the section was washed with PBS three times for 5 min, reacted with the fluorescent anti-mouse IgG antibody as the secondary antibody for 10 min, and examined for fluorescent images under a microscope.

As a result of a series of operations described above, the presence of various proteins in lacrimal gland tissues derived from patients with Sjôgren's syndrome was identified, and most were found to be localized in particular areas as shown in Table 1.

First, the focal area (central area) of lymphocyte infiltration was stained with anti-CD4 antibody, indicating the localization of CD4$^+$ T cells in that area. These results were also confirmed under a microscope at high magnification. Furthermore, the peripheral area of acinus was not stained with anti-CD4 antibody, indicating the absence of CD4$^+$ T cells in this area.

Staining images with anti-ICAM-1 antibody were also observed in the focal area of lymphocyte infiltration with a similar intensity as those with anti-CD4 antibody, indicating the localization of ICAM-1 in this focal area.

Staining images with anti-LFA-1 antibody were observed also in the focal area of lymphocyte infiltration with similar intensity as those with the above described anti-CD4 antibody and anti-ICAM-1 antibody, indicating the localization of LFA-1 in this focal area.

Staining images with anti-HLA-DR antibody were observed in both of the focal area of lymphocyte infiltration and the peripheral area of acini, indicating the presence of HLA-DR in both areas.

On the other hand, staining images with anti-CD8 antibody were observed in the peripheral area of acini, indicating the presence of CD8$^+$ T cells in this area. In addition, faint staining images were observed in the focal area of lymphocyte filtration under the microscope at a high magnification, indicating the presence of CD8$^+$ T cells in minute quantity also in the focal area.

Staining images with anti-integrin-$\alpha^E\beta_7$ antibody were observed mainly in the peripheral area of acini as those with anti-CD8 antibody, indicating the localization of $\alpha^E\beta_7{}^+$ T cells in that peripheral area.

Staining images with anti-E-cadherin antibody were observed on the whole membrane surface of acinar cells, indicating the presence of E-cadherin on the whole membrane area of said cells.

TABLE 1

Localization of various adhesion factors in the lacrimal gland tissue

|  | Focal area | Peripheral area |
|---|---|---|
| CD4 | +++ | − |
| ICAM-1 | +++ | − |
| LFA-1 | +++ | − |
| HLA-DR | + | + |
| CD8 | + | +++ |
| $\alpha^E\beta_7$ | − | ++ |
| E-cadherin | − | +++ |

From the results shown in Table 1, it was expected that CD4$^+$ T cells infiltrating into the focal area adhere to ICAM-1 of lacrimal gland cells mediated by LFA-1, and that CD8+ T cells infiltrating into the peripheral area of acini adhere to E-cadherin of lacrimal gland cells mediated by integrin $\alpha^E\beta_7$.

2) Specific adhesion of integrin $\alpha^E\beta_7^+$ T cells to lacrimal gland cells from patients with Sjôgren's syndrome Next, the number of integrin $\alpha^E\beta_7^+$ T cells adhering to acinar cells of lacrimal gland from patients with Sjôgren's syndrome was counted. Lacrimal gland cells from patients with dry eye symptom of non-Sjôgren's syndrome served as the control. Although these patients with dry eye of non-Sjôgren's syndrome manifest similar symptoms to those of patients with Sjôgren's syndrome, it has been proved, as described below, that dry eye of the former syndrome is caused by a different mechanism from that of Sjôgren's syndrome.

This measurement was performed according to the above described immunofluorescence staining technique. That is, a series of procedures were carried out similarly as described above using sections of lacrimal gland tissues from dry eye patients with both Sjôgren's and non-Sjôgren's syndromes as the starting material and anti-integrin $\alpha^E\beta_7$ antibody as the primary antibody. After imaging the staining results, plural lacrimal gland cells were selected to count the number of integrin $\alpha^E\beta_7^+$ T cells adhering to each, and the average the sum of the counted numbers divided by the number of selected cells was used as the measured value.

In Table 2 are shown the results of this measurement. Numbers of integrin $\alpha^E\beta_7^+$ T cells individually adhering to each one acinar cell from six dry eye patients with Sjôgren's syndrome and 5 dry eye patients with non-Sjôgren's syndrome were counted.

It was demonstrated that, in all but one of the patients with Sjôgren's syndrome, approximately 2.5 to 4.6 integrin $\alpha^E\beta_7^+$ T cells adhered to one acinar cell. In contrast, in dry eye patients with non-Sjôgren's syndrome, the number was about 0.4, even in one patient showing the adherence of $\alpha^E\beta_7$-bearing cells. These results clearly indicated that the number of integrin $\alpha^E\beta_7^+$ T cells adhering to each one acinar cell in patients with Sjôgren's syndrome was about 10 times higher than in those without non-Sjôgren's syndrome.

TABLE 2

Number of $\alpha^E\beta_7^+$ T cells adhering to one acinar cell in the lacrimal gland tissue tissue

| Patient | Number of $\alpha^E\beta_7^+$ T cells |
|---|---|
| With Sjôgren's syndrome | |
| 1 | 3.3 ± 0.367 |
| 2 | 4.6 ± 0.452 |
| 3 | 3.1 ± 0.4 |
| 4 | 3.9 ± 0.233 |
| 5 | 0 |
| 6 | 2.5 ± 0.5 |
| Non-Sjôgren's syndrome | |
| 1 | 0.4 ± 0.4 |
| 2 | 0.3 ± 0.213 |
| 3 | 0 |
| 4 | 0 |
| 5 | 0.4 ± 0.163 |

3) Specific adherence of other T cells to acinar cells from patients with Sjôgren's syndrome As described above, adherence of other T cells to acinar cells was comparatively examined using acinar cells from patients with Sjôgren's syndrome and from dry eye patients without Sjôgren's syndrome. Other lymphocytes used were CD4$^+$ T cells and CD8$^+$ T cells. In addition, integrin $\alpha^E\beta_7^+$ T cells were also used for comparison. Measurement of number of adhering cells was carried out similarly as described above using the immunofluorescence staining technique.

The results are shown in Table 3. The number of total adhering lymphocytes per one acinar cell in patients with Sjôgren's syndrome was 6.3±1.5, out of which the number of adhering CD4$^+$ T cells being 0.6±0.9.

The number of adhering CD8$^+$ T cells was 5.8±2.1, corresponding to about 10 times as much as that of adhering CD4$^+$ T cells, indicating that the destruction of acinar cells in patients with Sjôgren's syndrome is mainly caused by CD8$^+$ T cells. In addition, out of these CD8$^+$ T cells, the number of integrin $\alpha^E\beta_7^+$ T cells was 3.5±0.4.

In contrast, the number of adhering lymphocytes per acinar cell in patients with non-Sjôgren's syndrome (dry eye) was as low as less than 0.1 for any of CD4$^+$ T cells, CD8$^+$ T cells and integrin $\alpha^E\beta_7^+$ T cells.

TABLE 3

Number of various lymphocytes adhering to each acinar cell in salivary gland tissue

| Patient | Total lymphocytes | CD4$^+$ T cell | CD8$^+$ T cell | $\alpha^E\beta_7^+$ T cell |
|---|---|---|---|---|
| Sjôgren's syndrome | 6.3 ± 1.5 | 0.6 ± 0.9 | 5.8 ± 2.1 | 3.5 ± 0.4 |
| Non-Sjôgren's syndrome | <0.1 | <0.1 | <0.1 | <0.1 |

The above results indicated that the number of lymphocytes adhering to acinar cells is higher in patients with Sjôgren's syndrome as compared with those without Sjôgren's syndrome. In addition, in patients with Sjôgren's syndrome, lymphocytes adhering to acinar cells were mainly CD8+ T cells. Furthermore, it was indicated that more than half of these CD8$^+$ T cells adhere mediated by integrin $\alpha^E\beta_7$, and exerted cytotoxicity on acinar cells.

Example 2

Inhibition of Adherence Between Glandular Cells and Lymphocytes

As described above, it was indicated that, in patients with Sjôgren's syndrome, CD8$^+$ T cells adhere mainly mediated by integrin $\alpha^E\beta_7$, causing cytotoxicity to acinar cells.

Then, in order to prove that adherence between acinar cells and lymphocytes is mediated by the adherence between E-cadherin and integrin $\alpha^E\beta_7$, it was attempted to inhibit the adherence between those cells using anti-integrin $\alpha^E\beta_7$ antibody or anti-E-cadherin antibody.

Inhibitory experiments of cell adhesion was carried out according to those described in Journal of Immunology, 150, 3459–3470 (1993). That is, lacrimal gland cells were distributed into 12-well plates, and grown to reach confluence. $\alpha^E\beta_7^+$ T cells used were lymphocytes which had been prepared from the human peripheral blood and stimulated with PHA (phytohemagglutinin) for more than one week.

Either anti-E-cadherin antibody or anti-ICAM-1 antibody was added to each well containing confluent salivary gland cells and reacted at 37° C. for 5 min. These antibodies were all monoclonal and were diluted 50 times prior to use. In addition, either anti-integrin $\alpha^E\beta_7$ antibody or anti-LFA-1 antibody was added to $\alpha^E\beta_7^+$ T cells, and the mixture was incubated at 4° C. for 5 min. After the reaction, to each well containing salivary gland cells were added the antibody-treated $\alpha^E\beta_7^+$ T cells, and the mixture was incubated at 37° C. for 40 min. Then, after non-adhering lymphocytes were removed by gently washing with PBS, the cell cultures in each well were fixed with acetone, further washed, and then stained with toluidine blue. Staining images were inspected under a microscope to count the number of lymphocytes adhering to salivary gland cells. The results are shown in FIG. 1.

As a control, similar reactions to the above were carried out using a reaction solution containing no antibody, and the number of lymphocytes adhering to salivary gland cells under these conditions was taken as 100(%).

As shown in FIG. 1, after a series of reactions performed using anti-ICAM-1 antibody and anti-LFA-1 antibody, the number of lymphocytes adhering to salivary gland cells were about the same as that in the control.

On the other hand, after a series of reactions were carried out using anti-integrin $\alpha^E\beta_7$ antibody and anti-E-cadherin antibody, the number of lymphocytes adhering to salivary gland cells was reduced to 47% about half of that in the control. These results clearly indicated that the addition of anti-integrin $\alpha^E\beta_7$ antibody and anti-E-cadherin antibody results in the reduction of adherence of lymphocytes to salivary gland cells.

Furthermore, the reducing rate observed in these inhibition experiments matches well with the results obtained by the immunofluorescence staining technique using lacrimal gland cells. That is, from the results of immunofluorescence staining technique, it is assumed that about 55% of the total lymphocytes (about 3.5 integrin $\alpha^E\beta_7^+$ T cells/about 6.3 of total lymphocytes) adhering to lacrimal gland cells adhere mediated by $\alpha^E\beta_7$, and the adherence of remaining about 45% of them was mediated by adhesion factors other than $\alpha^E\beta_7$. These results are approximately the same as those of experiments on adherence inhibition described above using anti-$\alpha^E\beta_7$ antibody.

The above described results clearly indicated that the adherence of lymphocytes to salivary gland cells mediated by integrin $\alpha^E\beta_7$ can be inhibited almost completely using either anti-integrin $\alpha^E\beta_7$ antibody or anti-E-cadherin antibody.

In addition, it was demonstrated that the numbers of integrin $\alpha^E\beta_7^+$ T cells adhering to acinar cells in both lacrimal and salivary glands were about the same, indicating that these cells are destructed by similar mechanisms.

Furthermore, even though anti-integrin $\alpha^E\beta_7$ antibody or anti-E-cadherin antibodies were used, the adherence of lymphocytes to acinar cells could not be completely inhibited, indicating the presence of different adhesion factors. Therefore, those skilled in the art will be able to inhibit the adherence of lymphocytes to acinar cells completely by performing the above described series of reactions to detect these adhesion factors, and using antibodies raised against these factors as described above.

Example 3

Applications

The results described above indicate a possibility for attempting the mitigation and prevention of various disorders (for example, dry eyes, sialaporia, etc.) caused by the destruction of acinar cells in patients with the autoimmune adenitis of such as Sjôgren's syndrome through applications of anti-integrin $\alpha^E\beta_7$ antibody or anti-E-cadherin antibody as pharmaceutic.

For this purpose, anti-integrin $\alpha^E\beta_7$ antibody or anti-E-cadherin antibody, preferably monoclonal antibodies having the binding sites for both integrin $\alpha^E\beta_7$ and E-cadherin as the mutual recognition sites are used. Based on integrin $\alpha^E\beta_7$ or E-cadherin proteins, these antibodies can be formed, for example, according to the method described in Eur. J. Immunol., 24, 2832–2841 (1994). Alternatively, as anti-integrin $\alpha^E\beta$antibody may be used a commercial anti-CD103 (Pharmacia, Inc.), and as anti-E-cadherin antibody an anti-E-cadherin (Immunotech, Inc., France).

In order to apply the above described anti-integrin $\alpha^E\beta_7$ antibody or anti-E-cadherin antibody for pharmaceutic, appropriate excipients or bases prior to use depending on the application sites or pharmaceutical forms (such as injection, eye drop, tablet, etc.) may be added or compounded.

Also, anti-integrin $\alpha^E\beta_7$ antibody or anti-E-cadherin antibody may be used after modifying its carbohydrate chain to increase the absorption rate, etc. in humans.

As described above, the present invention has elucidated not only the adhesion factors involved in the adherence of lymphocytes to acinar cells in the autoimmune adenitis, but also their destruction mechanisms. Furthermore, this invention also elucidated the adhesion inhibitors capable of suppressing the adherence between lymphocytes and acinar cells which is the key mechanism of this cytotoxicity, making it possible to treat and prevent autoimmune adenitis by use of these adhesion inhibitors.

What is claimed is:

1. A method of inhibiting adhesion of lymphocytes to glandular cells that are lacrimal gland cells or salivary gland cells comprising exposing said lymphocytes and glandular cells to a specific inhibitor, wherein said inhibitor suppresses the adhesion of integrin of lymphocytes to E-cadherin of glandular cells, wherein said inhibitor is an antibody that binds to $\alpha^E\beta_7$ integrin of lymphocytes.

2. The method of claim 1, wherein said adhesion of lymphocytes to glandular cells causes autoimmune adenitis.

3. The method of claim 2, wherein said autoimmune adenitis is that in Sjôgren's syndrome.

4. The method of claim 3, wherein said adenitis in Sjôgren's syndrome comprises alacrima.

5. The method of claim 1, further comprising exposing said lymphocytes and glandular cells to an antibody that binds to E-cadherin of glandular cells.

6. A method of inhibiting adhesion of lymphocytes to glandular cells comprising exposing said lymphocytes and glandular cells to a specific inhibitor, wherein said inhibitor suppresses the adhesion of integrin of lymphocytes to E-cadherin of glandular cells, wherein said inhibitor is an antibody that binds to $\alpha^E\beta_7$ integrin of lymphocytes and wherein the adhesion of lymphocytes to said glandular cells causes autoimmune adenitis.

7. The method of claim 6, wherein said autoimmune adenitis is that in Sjôgren's syndrome.

8. The method of claim 7, wherein said adenitis in Sjôgren's syndrome comprises alacrima.

9. The method of claim 1, wherein said lymphocytes comprise CD8+T cells.

* * * * *